United States Patent
Klein

(10) Patent No.: US 10,383,891 B2
(45) Date of Patent: Aug. 20, 2019

(54) COMPOSITIONS COMPRISING SULFATED POLYSACCHARIDES AND USES THEREOF

(71) Applicant: ALGAMED THERAPEUTICS (A.M.T) LTD, Rosh Pina (IL)

(72) Inventor: Ronnie Klein, Haifa (IL)

(73) Assignee: ALGAMED THERAPEUTICS (A.M.T) LTD., Rosh Pina (IL)

( * ) Notice: Subject to any disclaimer, the term of this patent is extended or adjusted under 35 U.S.C. 154(b) by 13 days.

(21) Appl. No.: 15/095,475

(22) Filed: Apr. 11, 2016

(65) Prior Publication Data

US 2016/0220601 A1 Aug. 4, 2016

Related U.S. Application Data

(63) Continuation-in-part of application No. PCT/IL2015/050993, filed on Oct. 6, 2015.
(Continued)

(51) Int. Cl.
| | |
|---|---|
| C08B 37/00 | (2006.01) |
| A61K 31/737 | (2006.01) |
| A61K 45/06 | (2006.01) |
| A61K 47/36 | (2006.01) |
| A61K 31/352 | (2006.01) |
| A61K 31/4745 | (2006.01) |
| A61K 36/04 | (2006.01) |
| A61K 9/00 | (2006.01) |
| A61K 9/06 | (2006.01) |
| A61K 31/353 | (2006.01) |
| A61K 31/7028 | (2006.01) |
| A61K 36/03 | (2006.01) |
| A61K 36/05 | (2006.01) |
| A61K 36/22 | (2006.01) |
| A61K 36/23 | (2006.01) |
| A61K 36/28 | (2006.01) |
| A61K 36/42 | (2006.01) |
| A61K 36/45 | (2006.01) |
| A61K 36/48 | (2006.01) |
| A61K 36/53 | (2006.01) |
| A61K 36/537 | (2006.01) |
| A61K 36/55 | (2006.01) |
| A61K 36/752 | (2006.01) |

(Continued)

(52) U.S. Cl.
CPC .......... *A61K 31/737* (2013.01); *A61K 9/0034* (2013.01); *A61K 9/06* (2013.01); *A61K 31/352* (2013.01); *A61K 31/353* (2013.01); *A61K 31/4745* (2013.01); *A61K 31/7028* (2013.01); *A61K 36/03* (2013.01); *A61K 36/04* (2013.01); *A61K 36/05* (2013.01); *A61K 36/22* (2013.01); *A61K 36/23* (2013.01); *A61K 36/28* (2013.01); *A61K 36/42* (2013.01); *A61K 36/45* (2013.01); *A61K 36/48* (2013.01); *A61K 36/53* (2013.01); *A61K 36/537* (2013.01); *A61K 36/55* (2013.01); *A61K 36/752* (2013.01); *A61K 36/82* (2013.01); *A61K 36/87* (2013.01); *A61K 36/886* (2013.01); *A61K 45/06* (2013.01); *A61K 47/12* (2013.01); *A61K 47/183* (2013.01); *A61K 47/22* (2013.01); *A61K 47/26* (2013.01); *A61K 47/32* (2013.01); *A61K 47/36* (2013.01); *A61K 47/42* (2013.01); *A61P 15/02* (2018.01); *C08B 37/006* (2013.01)

(58) Field of Classification Search
None
See application file for complete search history.

(56) References Cited

U.S. PATENT DOCUMENTS

| | | | | |
|---|---|---|---|---|
| 5,466,463 | A * | 11/1995 | Ford | A61K 9/0034 424/433 |
| 7,078,392 | B2 * | 7/2006 | Zaneveld | A61K 9/0034 514/54 |

(Continued)

FOREIGN PATENT DOCUMENTS

| | | | | |
|---|---|---|---|---|
| DE | 3516398 | | 11/1986 | |
| DE | 10329361 | * | 1/2005 | ............... A61K 7/48 |

(Continued)

OTHER PUBLICATIONS

Shahrzad et al., "Pharmacokinetics of Gallic Acid and Its Relative Bioavailability from Tea in Healthy Humans" The Journal of Nutrition (2001) vol. 131 pp. 1207-1210 (Year: 2001).*

(Continued)

*Primary Examiner* — Eric Olson
(74) *Attorney, Agent, or Firm* — Pearl Cohen Zedek Latzer Baratz LLP

(57) ABSTRACT

The present invention relates to a composition for intravaginal and/or for internal mucosal application, comprising an effective amount of a sulfated polysaccharide, one or more of a natural quaternary polymer, a quaternary molecular compound, a metalloproteinase inhibitor, one or more anti-inflammatory agent, an acid pH control buffering system or any combination thereof, and a pharmaceutically acceptable carrier. The invention is further related to a method of treating or alleviating vaginal infection, vaginal dryness, vaginal or vulvo vaginal atrophy, vaginal itching, dyspareunia, vaginal or vulvar pain, vaginal or perivaginal inflammation or for promoting vaginal or wound healing, vaginal atrophy/dryness caused by radiotherapy, chemotherapy and/or hormonal treatment and decreased vaginal boundary lubrication or a disease or condition associated therewith or of improving vaginal boundary lubrication.

6 Claims, 1 Drawing Sheet

Related U.S. Application Data

(60) Provisional application No. 62/060,054, filed on Oct. 6, 2014.

(51) Int. Cl.
　　*A61K 36/82*　　(2006.01)
　　*A61K 36/87*　　(2006.01)
　　*A61K 36/886*　　(2006.01)
　　*A61K 47/12*　　(2006.01)
　　*A61K 47/18*　　(2017.01)
　　*A61K 47/22*　　(2006.01)
　　*A61K 47/26*　　(2006.01)
　　*A61K 47/32*　　(2006.01)
　　*A61K 47/42*　　(2017.01)
　　*A61P 15/02*　　(2006.01)

(56) References Cited

U.S. PATENT DOCUMENTS

| | | | | |
|---|---|---|---|---|
| 8,349,368 | B2 * | 1/2013 | Gordon | A61K 31/198 424/659 |
| 8,673,375 | B2 * | 3/2014 | Hill | A61K 36/58 424/725 |
| 9,453,082 | B2 * | 9/2016 | Bavington | A61K 36/05 |
| 2005/0239742 | A1 | 10/2005 | Place | |
| 2010/0256089 | A1 | 10/2010 | Maguire | |

FOREIGN PATENT DOCUMENTS

| | | | |
|---|---|---|---|
| WO | WO2006/091180 | * | 8/2006 |
| WO | WO2010061284 | | 6/2010 |

OTHER PUBLICATIONS

"Quercetin Food Chart" downloaded Sep. 14, 2017 from http://www.quercetin.com/overview/food-chart (Year: 2017).*

English machine translation of DE10329361, downloaded May 1, 2018 from translationportal.epo.org (Year: 2018).*

Guardia et al., "Anti-inflammatory properties of plant flavonoids. Effects of rutin, quercetin and hesperidin on adjuvant arthritis in rat" Il farmaco (2001) vol. 56 pp. 683-687 (Year: 2001).*

Kroes et al., "Anti-Inflammatory Activity of Gallic Acid" Planta Mdeica (1992) vol. 58 pp. 499-504 (Year: 1992).*

Huheihel et al., "Activity of *Porphyridium* sp. polysaccharide against herpes simplex viruses in vitro and in vivo" J Biochem Biophys Methods vol. 50 pp. 189-200 (Year: 2002).*

International Search Report for PCT application No. PCT/IL2015/050993 dated Jan. 11, 2016.

Rossi, S., et al. "Associations of natural polymers to modulate mucoadhesion of vaginal rinse-off and leave-on formulations." Journal of Drug Delivery Science and Technology 24.5 (2014): 435-560.

* cited by examiner

COMPOSITIONS COMPRISING SULFATED POLYSACCHARIDES AND USES THEREOF

This application is a continuation-in-part of PCT International Application No. PCT/IL2015/050993, international filing date Oct. 6, 2015, entitled "Compositions comprising sulfated polysaccharides and uses thereof", which in turn claims priority from U.S. Provisional application 62/060,054, filed Oct. 6, 2014, both of which are incorporated herein by reference.

FIELD OF THE INVENTION

The present invention relates to compositions comprising sulfated polysaccharides and uses thereof.

BACKGROUND OF THE INVENTION

According to the world health organization (WHO), reproductive and sexual ill-health accounts for 20% of the global sickness in women and therefore advances in women's health are a necessity.

Women's health considerations may encompass issues such as fertility, sexually transmitted diseases, local reproductive tract infections and neoplasms, pregnancy, as well as perimenopause and post-menopause care. Perimenopause and post-menopause symptoms as well as breast feeding, anti-hormonal therapy and contraceptive pills may include vaginal and vulvar pain, irritation, burning, itching, discharge, dyspareunia.

Atrophic vaginitis is a hormone-dependent disease involving the genital tract and lower urinary tract. Atrophic vaginitis occurs during or after menopause, and its symptoms increase with age. Due to estrogen loss, the vagina is shortened narrowed, and the vaginal walls become thinner and less elastic. Dyspareunia, burning and chronic vaginitis do not disappear with time. Further, vaginal dryness occurs. The vaginal surface becomes friable, with petechiae, ulcerations, and bleeding often occurring after minimal trauma.

Chemotherapy, radiotherapy and hormonal therapy (in particular aromatase inhibitors) in cancer patients can lead to vaginal atrophy and/or dryness.

Simple and safe treatments for these conditions are limited, and to date there has been no single simple platform to address women's reproductive health issues.

SUMMARY OF THE INVENTION

One object of the present invention to provide a composition for intravaginal application, comprising sulfated polysaccharides and use thereof for promoting women's reproductive health.

In some aspects of this invention, there is provided a composition for intravaginal application, comprising sulfated polysaccharides. In some embodiments of the invention, the composition for intravaginal and/or for internal mucosal application, comprises an effective amount of a sulfated polysaccharide, one or more of a natural quaternary polymer, a quaternary molecular compound, a metalloproteinase inhibitor, an anti-inflammatory agent, an acid pH control buffering system or any combination thereof, and a pharmaceutically acceptable carrier.

In some embodiments, the sulfated polysaccharides from at least one alga, which may be red, brown or green is characterized by a percent sulfation of the polysaccharide chain of between 3-35%. According to an embodiment of the invention, the percent of sulfation is between 3-10% of the polysaccharide chain. According to an embodiment of the invention, the percent of sulfation is between 3-4% of the polysaccharide chain. According to an embodiment of the invention, the percent of sulfation is between 4-5% of the polysaccharide chain. According to an embodiment of the invention, the percent of sulfation is between 5-6% of the polysaccharide chain. According to an embodiment of the invention, the percent of sulfation is between 6-7% of the polysaccharide chain. According to an embodiment of the invention, the percent of sulfation is between 7-8% of the polysaccharide chain. According to an embodiment of the invention, the percent of sulfation is between 8-9% of the polysaccharide chain. According to an embodiment of the invention, the percent of sulfation is between 9-10% of the polysaccharide chain. According to an embodiment of the invention, the percent of sulfation is between 10-35% of the polysaccharide chain.

In some embodiments, the at least one red microalga sulfated polysaccharide is characterized by having a glucuronic acid chain segment in the sulfated polysaccharide polymer in an amount of at least 4%. In some embodiment, the amount of the glucuronicacid chain segment is between 4-15%. In some embodiments, the amount of the glucuronic acid chain segment is between 4-7%. In some embodiment, the amount of the glucuronic acid chain segment is between 7-8%. In some embodiment, the amount of the glucuronic acid chain segment is between 8-9%. In some embodiment, the amount of the glucuronic acid chain segment is between 9-10%. In some embodiment, the amount of the glucuronic acid chain segment is between 10-11%. In some embodiment, the amount of the glucuronic acid chain segment is between 11-12%. In some embodiment, the amount of the glucuronic acid chain segment is between 12-13%. In some embodiment, the amount of the glucuronic acid chain segment is between 13-14%. In some embodiment, the amount of the glucuronic acid chain segment is between 14-15%.

In some embodiments of the invention, the composition further comprises one or more of a moisturizing agent, a chelating agent, a lubricant, a preservative or any combination thereof.

In some embodiments of the invention, the composition further comprises water.

In some embodiments of the invention, the sulfated polysaccharide is characterized by a percent sulfation of the polymeric chain between 0.01-32%.

In some embodiments of the invention, the sulfated polysaccharide is in an amount of 0.01-10% wt/wt of the solution.

In some embodiments of the invention, the composition further comprises one or more of an antimicrobial, an antiviral, an antifungal, an anti-inflammatory, anti-irritating, anti-itching, a hormone or a spermicidal compound.

In some embodiments of the invention, the composition may be used in the manufacture of a medicament for treating vaginal infection, vaginal dryness, vaginal or vulvo vaginal atrophy, vaginal itching, dyspareunia, vaginal or vulvar pain, vaginal or perivaginal inflammation or for promoting vaginal wound healing.

In some embodiments of the invention, the composition may be used in the manufacture of a medicament for treating or alleviating decreased vaginal boundary lubrication or a disease or condition associated therewith or of improving vaginal boundary lubrication.

In some embodiments of the invention, the disease or the condition associated with decreased vaginal boundary lubrication is vaginal atrophy, dyspareunia, Sjogren's syndrome, menopause, androgen deficiency, estrogen deficiency, estrogen replacement therapy, allergy, chronic inflammation, menopause, premature menopause, chemotherapy, hormonal therapy for cancer patients (specially aromatase inhibitors), breastfeeding, surgical removal of the ovaries before menopause, genital lichen sclerosis, vulvodynia, bacterial vaginosis, herpes, candida, psoriasis, contact dermatitis, condylomata, or side effects of medications and aging.

In some embodiments of the invention, the composition may be used in the manufacture of a medicament for preventing episiotomy or for treating tissue damages after episiotomy wherein if used for preventing episiotomy, the composition of the administered a week, two weeks, three weeks or a month before the date of delivery of a newborn.

In some embodiments of the invention, the composition comprises an effective amount of a natural quaternary polymer or a quaternary molecular compound. In some embodiments of the invention, the quaternary molecular compound is laurylpyridinium chloride, cetylpyridiniun chloride, hydroxypropyltrimonium hydrolyzed proteins, hydroxypropyl guar hydroxypropyltrimonium chloride, beta glucan hydroxypropyltrimonium chloride or berberine.

In some embodiments of the invention, the composition comprises chitosan

In some embodiments of the invention, the sulfated polysaccharide is characterized by a percent sulfation of the polymeric chain of between 4-35%.

Embodiments of the invention are directed to a composition for intravaginal and/or for internal mucosal application, comprising an effective amount of a sulfated polysaccharide, one or more of a natural quaternary polymer, a quaternary molecular compound, a metalloproteinase inhibitor, one or more anti-inflammatory agent, an acid pH control buffering system or any combination thereof, and a pharmaceutically acceptable carrier.

According to some embodiments, the sulfated polysaccharide is derived from alga. According to some embodiments, the alga is a red alga, green alga and/or a brown alga. According to further embodiments, the red alga is *Porphyridium* sp., *P. aerugineum*, *Porphyridium Cruentum*, *porphyridium purpureum*, *R. reticulata. Cyanidioschyzon merolae*, *Atractophora hypnoides*, *Gelidiella calcicola*, *Lemanea*, *Palmaria palmata*, *Schmitzia hiscockiana*, *Chondrus crispus*, *Mastocarpus stellatus*, and/or *Acrochaetium efflorescens*. The brown alga is in some embodiments, *Undaria pinnatifida*, *Larninaria saccharina. L. digitata*, *Fucus evanescens. F. serratus*, *F. distichus*, *F. spiralis*, *Ascophylium nodosum* and/or *Fucus vesiculosus* and the green alga/cyanobacteria is in some embodiments *Prasinococcus capsulatus*, *Spirulina*, *Chlorella*, *Isochrysis* and/or *Dunaliella*.

According to some embodiments, the metalloproteinase inhibitor is one or more of soy isoflavone aglycone, Green tea (*Camellia sinensis*), Grape seed or Gotu Kola (*Centella asiatica*) extracts. According to some embodiments, the anti-inflammatory agent is one or more of Green tea (*Camellia sinensis*), Grape seed or Gotu Kola (*Centella asiatica*) extracts, sodium carboxymethyl betaglucan, *Chondrus Chrispus*, melissa, grape fruit, mango seed, cranberry, cucumber, salvia, chamomile, and aloevera.

According to some embodiments, the acid pH control buffering system is lactic acid, sodium dibasic hydrogen phosphate, sodium lactate, citric acid, or any combination thereof. According to some embodiments, the composition further comprises one or more of a moisturizing agent, a chelating agent, a lubricant, a preservative or any combination thereof. According to some embodiments, the moisturizing agent is saccharide isomerate, the lubricant is lubrasil DM hydrogel and the chelating agent is EDTA According to some embodiments, the composition further comprises one or more of extract of *Chondrus Chrispus*, Xanthan gum, caprylhydroxamic acid, caprylyl glycol, glycerin, undecylenic acid, allantoin, monoester of caprylic acid, an extract of any one of echinaccea, propolis, comfrey, melissa, grape fruit, mango seed, cranberry, cucumber, green tea, salvia, Chamomile, Geranium, lavender, lemon, juniper, clove bud, lotus, moringa, Grape seed or Gotu Kola (*Centella asiatica* extracts) or any combination thereof.

According to some embodiments, the composition further comprises water. According to some embodiments, the composition further comprises chitosan. According to some embodiments, the sulfated polysaccharide is characterized by a percent sulfation of the polymeric chain between 0.01-32%. According to some embodiments, the sulfated polysaccharide is in an amount of 0.01-10% wt/wt of the solution. According to some embodiments, the sulfated polysaccharide comprises a polymeric chain comprising at least 4% glucuronic acid. According to some embodiments, composition further comprises one or more of an antimicrobial, an antiviral, an antifungal, an anti-inflammatory, anti-irritating, anti-itching, growth factor, a hormone or a spermicidal compound.

According to some embodiments, the composition is in a form of a cream, an ointment, a solution, a gel, a suppository, an emulsion, a foam, a capsule, a pill or a tablet. According to some embodiments, the natural quaternary polymer is quaternary guar. According to some embodiments, the quaternary molecular compound is laurylpyridinium chloride, cetylpyridiniun chloride, hydroxypropyltrimonium hydrolyzed proteins, beta glucan hydroxypropyltrimonium chloride, berberine or Hydroxypropyl Guar Hydroxypropyltrimonium Chloride. According to some embodiments, sulfated polysaccharide is characterized by a percent sulfation of the polymeric chain of between 0.01-16%.

Embodiments of the invention are directed to a method for treating vaginal infection, vaginal dryness, vaginal or vulvo vaginal atrophy, vaginal itching, dyspareunia, vaginal or vulvar pain, vaginal or perivaginal inflammation or for promoting vaginal or wound healing or vaginal atrophy or dryness during or following chemotherapy or hormonal therapy comprising administering the composition as detailed herein.

Embodiments of the invention are directed to a method for treating or alleviating decreased vaginal boundary lubrication or a disease or condition associated therewith or of improving vaginal boundary lubrication comprising administering the composition as detailed herein.

According to some embodiments, the disease or the condition associated with decreased vaginal boundary lubrication is vaginal atrophy, dyspareunia, Sjogren's syndrome, menopause, androgen deficiency, estrogen deficiency, estrogen replacement therapy, allergy, chronic inflammation, menopause, premature menopause, chemotherapy, breastfeeding, surgical removal of the ovaries before menopause, genital lichen sclerosis, vulvodynia, bacterial vaginosis, herpes, candida, psoriasis, contact dermatitis, condylomata, or side effects of medications and aging.

Embodiments of the invention are directed to a method for preventing episiotomy or for treating tissue damages after episiotomy comprising administering a composition as detailed herein. According to some embodiments, if used for preventing episiotomy, the composition of the administered a week, two weeks, three weeks or a month before the date of delivery of a newborn.

Embodiments of the invention are directed to a method for preventing or for treating tissue damages associated with chemotherapy or hormonal therapy for cancer patients treated with drugs that block estrogen receptors, lowering estrogen level or progesterone-based agents comprising administering a composition as detailed herein. According to some embodiments, the hormonal therapy for cancer patients includes an aromatase inhibitor. According to some embodiments, the composition of the invention is administered during or at the end of a chemotherapy/hormonal treatment.

Embodiments of the invention are directed to a method for treating vaginal infection, vaginal dryness, vaginal or vulvo vaginal atrophy, vaginal itching, dyspareunia, vaginal or vulvar pain, vaginal or perivaginal inflammation or for promoting vaginal or wound healing, vaginal atrophy/dryness caused by radiotherapy, chemotherapy and/or hormonal treatment comprising administering a composition comprising an effective amount of a sulfated polysaccharide and a pharmaceutically acceptable carrier, wherein the composition is in a form for intravaginal application, internal mucosal application, or both.

Embodiments of the invention are directed to a method for treating or alleviating decreased vaginal boundary lubrication or a disease or condition associated therewith or of improving vaginal boundary lubrication comprising administering a composition comprising an effective amount of a sulfated polysaccharide and a pharmaceutically acceptable carrier, wherein the composition is in a form for intravaginal application, internal mucosal application, or both.

According to some embodiments, the disease or the condition associated with decreased vaginal boundary lubrication is vaginal atrophy, dyspareunia, Sjogren's syndrome, menopause, androgen deficiency, estrogen deficiency, estrogen replacement therapy, allergy, chronic inflammation, menopause, premature menopause, chemotherapy, breastfeeding, surgical removal of the ovaries before menopause, genital lichen sclerosis, vulvodynia, bacterial vaginosis, herpes, candida, psoriasis, contact dermatitis, condylomata, or side effects of medications and aging.

Embodiments of the invention are directed to a method for preventing episiotomy or for treating tissue damages after episiotomy comprising administering a composition comprising an effective amount of a sulfated polysaccharide and a pharmaceutically acceptable carrier, wherein the composition is in a form for intravaginal application, internal mucosal application, or both.

According to some embodiments, if administered for preventing episiotomy, the composition is administered for a week, two weeks, three weeks or a month before the date of delivery of a newborn.

Embodiments of the invention are directed to a method for preventing or treating vaginal atrophy or dryness during and following chemotherapy and/or hormonal therapy comprising administering a composition comprising an effective amount of a sulfated polysaccharide and a pharmaceutically acceptable carrier, wherein the composition is in a form for intravaginal application, internal mucosal application, or both. According to some embodiments, the hormonal therapy includes aromatase inhibitors.

According to some embodiments, the sulfated polysaccharide is derived from alga. According to some embodiments, the alga is a red alga, green alga and/or a brown alga. According to further embodiments, the red alga is *Porphyridium* sp., *P. aerugineum, Porphyridium Cruentum, porphyridium purpureum, R. reticulata. Cyanidioschyzon merolae, Atractophora hypnoides, Gelidiella calcicola, Lemanea, Palmaria palmata, Schmitzia hiscockiana, Chondrus crispus, Mastocarpus stellatus*, and/or *Acrochaetium efflorescens*. The brown alga is in some embodiments, *Undaria pinnatifida, Laminaria saccharine, L. digitata, Films evanescens, F. serratus, F. distichus, F. spiralis, Ascophyllum nodosum* and/or *Fucus vesiculosus* and the green alga/cyanobacteria is in some embodiments *Prasinococcus capsulatus, Spirulina, Chlorella, Isochrysis* and/or *Dunaliella*.

Embodiments of the invention are directed to a composition for intravaginal and/or for internal mucosal application, comprising an effective amount of a sulfated polysaccharide, one or more of a natural quaternary polymer, a quaternary molecular compound, a metalloproteinase inhibitor, one or more anti-inflammatory agent, an acid pH control buffering system or any combination thereof, and a pharmaceutically acceptable carrier.

According to some embodiments, the metalloproteinase inhibitor is one or more of soy isoflavone aglycone, Green tea (*Camellia sinensis*), Grape seed or Gotu Kola (*Centella asiatica*) or wherein the anti-inflammatory agent is one or more of Green tea (*Camellia sinensis*), Grape seed or Gotu Kola (*Centella asiatica*) extracts, sodium carboxymethyl betaglucan, *Chondrus Chrispus*, melissa, grape fruit, mango seed, cranberry, cucumber, salvia, chamomile, and aloe vera extracts.

According to some embodiments, the acid pH control buffering system is lactic acid, sodium dibasic hydrogen phosphate, sodium lactate, citric acid, or any combination thereof.

According to some embodiments, the composition further comprises one or more of saccharide isomerate as a moisturizing agent, ethylenediaminetetraacetic acid (EDTA) as a chelating agent, and lubrasil DM hydrogel as a lubricant. According to some embodiments, the composition further comprises one or more of extract of *Chondrus Chrispus*, Xanthan gum, caprylhydroxamic acid, caprylyl glycol, glycerin, undecylenic acid, allantoin, monoester of caprylic acid, an extract of any one of echinaccea, propolis, comfrey, melissa, grape fruit, mango seed, cranberry, cucumber, green tea, salvia, Chamomile, Geranium, lavender, lemon, juniper, clove bud, lotus, moringa, Grape seed or Gotu Kola (*Centella asiatica* extracts) or any combination thereof. According to some embodiments, the composition further comprises chitosan.

According to some embodiments, the sulfated polysaccharide is in an amount of 0.005-5% wt/wt of the solution. According to some embodiments, the sulfated polysaccharide comprises a polymeric chain comprising at least 4% glucuronic acid. According to some embodiments, the composition further comprises one or more of an antimicrobial, an antiviral, an antifungal, an anti-inflammatory, anti-irritating, anti-itching, growth factor, a hormone or a spermicidal compound. According to some embodiments, the composition is in a form of a cream, an ointment, a solution, a gel, a suppository, an emulsion, foam, a capsule, a pill or a tablet.

According to some embodiments, the natural quaternary polymer is Guar Hydroxypropyltrimonium Chloride. According to some embodiments, the quaternary molecular compound is laurylpyridinium chloride, cetylpyridiniun chloride, hydroxypropyltrimonium hydrolyzed proteins, beta glucan hydroxypropyltrimonium chloride, berberine or Hydroxypropyl Guar Hydroxypropyltrimonium Chloride.

Embodiments of the invention are further directed to a method for treating or alleviating decreased vaginal boundary lubrication or a disease or condition associated therewith or of improving vaginal boundary lubrication, vaginal damages, vaginal infection, vaginal dryness, vaginal or vulvo vaginal atrophy, vaginal itching, dyspareunia, vaginal or vulvar pain, vaginal or perivaginal inflammation or for promoting vaginal or wound healing, vaginal atrophy/dryness caused by radiotherapy, chemotherapy and/or hormonal treatment comprising administering a composition comprising an effective amount of a sulfated polysaccharide and a pharmaceutically acceptable carrier, wherein the composition is in a form for intravaginal application, internal mucosal application, or both.

According to some embodiments, the disease or the condition associated with decreased vaginal boundary lubrication is vaginal atrophy, dyspareunia, Sjogren's syndrome, menopause, androgen deficiency, estrogen deficiency, estrogen replacement therapy, allergy, chronic inflammation, menopause, premature menopause, chemotherapy, breastfeeding, surgical removal of the ovaries before menopause, genital lichen sclerosis, vulvodynia, bacterial vaginosis, herpes, candida, psoriasis, contact dermatitis, condylomata, or side effects of medications and aging.

Further embodiments are directed to a method for preventing episiotomy or for treating tissue damages after episiotomy comprising administering a composition comprising an effective amount of a sulfated polysaccharide and a pharmaceutically acceptable carrier, wherein the composition is in a form for intravaginal application, internal mucosal application, or both.

According to some embodiments, if administered for preventing episiotomy, the composition is administered for a week, two weeks, three weeks or a month before the date of delivery of a newborn.

Further embodiments are directed to a method for preventing or treating vaginal damages, atrophy or dryness during and following chemotherapy and/or hormonal therapy for cancer patients treated with drugs that block estrogen receptors, lowering estrogen level or progesterone-based agents comprising administering a composition comprising an effective amount of a sulfated polysaccharide and a pharmaceutically acceptable carrier, wherein the composition is in a form for intravaginal application, internal mucosal application, or both, wherein the hormonal therapy includes aromatase inhibitors.

According to some embodiments, the sulfated polysaccharide is derived from alga. According to some embodiments, the alga is a red alga, green alga and/or a brown alga. According to further embodiments, the red alga is *Porphyridium* sp., *P. aerugineum, Porphyridium Cruentum, porphyridium purpureum, R. reticulata. Cyanidioschyzon merolae, Atractophora hypnoides, Gelidiella calcicola, Lemanea, Palmaria palmata, Schmitzia hiscockiana, Chondrus crispus, Mastocarpus stellatus*, and/or *Acrochaetium efflorescens*. The brown alga is in some embodiments, *Undaria pinnatifida, Laminaria saccharina, L. digitata, Fucus evanescens, F. serratus, F. distichus, F. spiralis, Ascophyllum nodosum* and/or *Fucus vesiculosus* and the green alga/cyanobacteria is in some embodiments *Prasinococcus capsulatus, Spirulina, Chlorella, Isochrysis* and/or *Dunaliella*.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features and advantages thereof, may best be understood by reference to the following detailed description when read with the accompanied drawings. Embodiments of the invention are illustrated by way of example and not limitation in the figures of the accompanying drawings, in which like reference numerals indicate corresponding, analogous or similar elements, and in which:

DETAILED DESCRIPTION OF THE INVENTION

Figure 1:
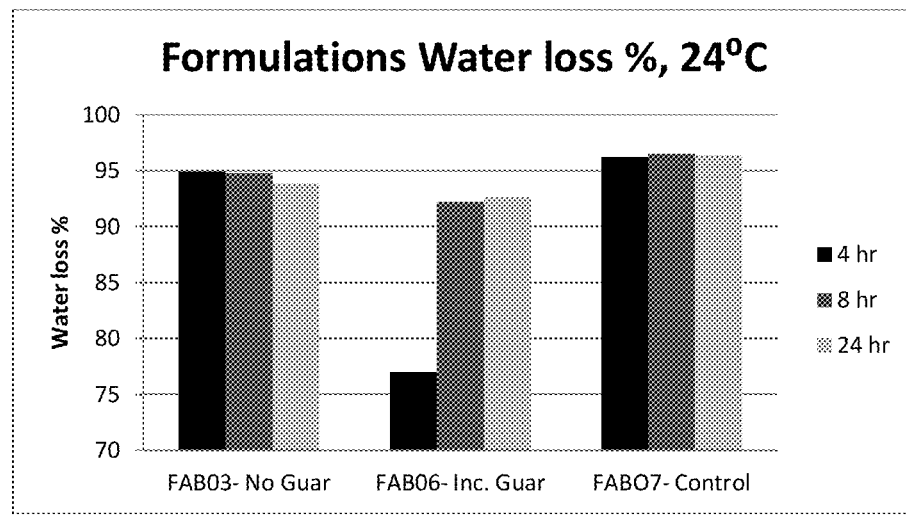
FIG. 1 presents the water loss of three formulations as measured at three different time points, after incubation at 24° C.

It is noted that throughout, all ranges and numeric figures are considered to be approximate even when the term "about" is not used, such that the document is considered to cover ±10% of the disclosed range or figure, unless specifically mentioned otherwise. It is further noted that the term "about" is also considered to cover ±10% of the disclosed range or figure, unless specifically mentioned otherwise.

It is further noted that throughout, the terms immune enhancing and anti-inflammatory are interchangeable.

In some aspects of this invention, there is provided a composition for intravaginal application comprising sulfated polysaccharides.

According to some embodiments of the invention, there is provided a composition for intravaginal and/or for internal mucosal application, comprising an effective amount of a sulfated polysaccharide and one or more of a natural quaternary polymer, a quaternary molecular compound, a metalloproteinase inhibitor, an anti-inflammatory agent, an acid pH control buffering system or any combination thereof. Further provided is a pharmaceutically acceptable carrier. The addition of a quaternium molecule or quaternary polymer to the polysaccharide may initiate a deposition process where, a homogenous, thin, longer lasting coating, a more intimately attachment of formula to the vaginal tissue is formed and the formulation has increased ability to retain water therefore, to hydrates and moisturizes the vaginal tissue. Cell wall membranes are usually negatively charged and a quaternary polymer is usually a cationic polymer or compound. The negative charge of the cell wall membranes attracts to positively charged quaternary molecules therefore allowing a longer lasting coating of formula with higher water content. In some embodiments of the invention, the addition of a quaternium molecule or quaternary polymer to the polysaccharide can reduce trans-epidermal water loss (TEWL) in the vaginal tissue and improve drug delivery.

In some embodiments of the invention, the quaternary compound is a polymeric quaternium ammonium salt of hydroxyemlcelulose, berberine, quaternary guar and/or Hydroxypropyl guar hydroxypropyltrimonium chloride.

In some embodiments of the invention, the natural quaternary polymer/quaternary molecular compound is hydroxypropyltrimonium hydrolyzed proteins or beta glucan hydroxypropyltrimonium chloride.

According to some embodiments of the invention the natural quaternary polymer or the quaternary molecular compound is presented in an amount of between 0.01-5.0% wt/wt. According to some embodiments of the invention the natural quaternary polymer or the quaternary molecular compound is presented in an amount of between 0.01-1.0% wt/wt. According to some embodiments of the invention the natural quaternary polymer or the quaternary molecular compound is presented in an amount of between 1.0-2.0% wt/wt. According to some embodiments of the invention the natural quaternary polymer or the quaternary molecular compound is presented in an amount of between 2.0-3.0% wt/wt. According to some embodiments of the invention the natural quaternary polymer or the quaternary molecular compound is presented in an amount of between 3.0-4.0% wt/wt. According to some embodiments of the invention the natural quaternary polymer or the quaternary molecular compound is presented in an amount of between 4.0-5.0% wt/wt.

According to some embodiments of the invention the natural quaternary polymer or the quaternary molecular compound is presented in an amount of between 0.1-5% wt/wt. According to some embodiments of the invention the natural quaternary polymer or the quaternary molecular compound is presented in an amount of between 0.1-1.0% wt/wt. According to some embodiments of the invention the natural quaternary polymer or the quaternary molecular compound is presented in an amount of between 1.0-2.0% wt/wt. According to some embodiments of the invention the natural quaternary polymer or the quaternary molecular compound is presented in an amount of between 2.0-3.0% wt/wt. According to some embodiments of the invention the natural quaternary polymer or the quaternary molecular compound is presented in an amount of between 3.0-4.0% wt/wt. According to some embodiments of the invention the natural quaternary polymer or the quaternary molecular compound is presented in an amount of between 4.0-5.0% wt/wt.

According to some embodiments of the invention the quaternary guar which may be hydroxypropyl guar hydroxypropyltrimonium chloride, is presented in an amount of between 0.2-5% wt/wt. According to some embodiments of the invention the quaternary guar is presented in an amount of between 0.2-1.0% wt/wt. According to some embodiments of the invention the quaternary guar is presented in an amount of between 1.0-2.0% wt/wt. According to some embodiments of the invention the quaternary guar is presented in an amount of between 2.0-3.0% wt/wt. According to some embodiments of the invention the quaternary guar is presented in an amount of between 3.0-4.0% wt/wt. According to some embodiments of the invention the quaternary guar is presented in an amount of between 4.0-5.0% wt/wt.

According to some embodiments of the invention the quaternary guar is presented in an amount of between 0.01-4.0% wt/wt. According to some embodiments of the invention the quaternary guar, which may be hydroxypropyl guar hydroxypropyltrimonium chloride, is presented in an amount of between 0.01-1.0% wt/wt. According to some embodiments of the invention the quaternary guar is presented in an amount of between 1.0-2.0% wt/wt. According to some embodiments of the invention the quaternary guar is presented in an amount of between 2.0-3.0% wt/wt. According to some embodiments of the invention the quaternary guar is presented in an amount of between 3.0-4.0% wt/wt. According to some embodiments of the invention the quaternary guar is presented in an amount of between 0.2-5% wt/wt. According to some embodiments, xanthan gum is present in an amount of between about 0.1-5%. According to some embodiments, xanthan gum is present in an amount of between about 0.1-1.0%. According to some embodiments, xanthan gum is present in an amount of between about 1.0-2.0%. According to some embodiments, xanthan gum is present in an amount of between about 2.0-3.0%. According to some embodiments, xanthan gum is present in an amount of between about 3.0-4.0%. According to some embodiments, xanthan gum is present in an amount of between about 4.0-5.0%.

In some embodiments of the invention, the quaternary molecular compound is an ammonium compound, wherein the quaternary nitrogen is in amine or amide form, possibly substituted with one or two alkyl groups, lauryl pyridinium chloride, cetylpyridiniun chloride, hydroxypropyltrimonium, hydrolyzed protein, such as oats, rice, bran, soy, and wheat (such as for example, hydroxypropyltrimonium hydrolyzed wheat protein), berberine, beta glucan hydroxypropyltrimonium chloride or hydroxypropyl guar hydroxypropyltrimonium chloride. In some embodiments of the invention, the metalloproteinase inhibitor is soy isoflavone aglycone. In some embodiments of the invention, the metalloproteinase inhibitor is Green tea extract, Gotu Kola (*Centalla asiatica*) extract, Grape seed extract, ursolic acid, rosmarinic acid or soy isoflavone aglycone, or any combination thereof. In some embodiments of the invention, there is a synergy between the sulfated polysaccharide and the metallproteinase inhibitor in treating inflammation, reducing irritation and/or strengthening the vaginal tissue.

According to some embodiments of the invention, the anti-inflammatory agent is sodium carboxymethyl betaglucan (CM Beta glucan). In some embodiments of the invention, the anti-inflammatory agent is Green tea extract, Gotu Kola (*Centalla asiatica*) extract, Grape seed extract, sodium carboxymethyl betaglucan, epicatechin, glycyrrhiza, resveratrol (polyphenol), *Chondrus Chrispus*, melissa, grape fruit, mango seed, cranberry, cucumber, salvia, chamomile, aloevera or a combination thereof. In some embodiments of the invention, there is a synergy between the sulfated polysaccharide and the sodium carboxymethyl betaglucan, epicatechin, glycyrrhiza, Green tea extract, Gotu Kola (*Centalla asiatica*) extract, Grape seed extract *Chondrus Chrispus*, melissa, grape fruit, mango seed, cranberry, cucumber, salvia, chamomile, aloevera and/or the resveratrol or the combination thereof in treating inflammation and/or irritation.

According to some embodiments of the invention, the acid pH control buffering system is lactic acid, sodium lactate, citric acid, acetic acid, sorbic acid, propionic acid, sodium dibasic hydrogen phosphate or any combination thereof.

In some embodiments of the invention, the composition for intravaginal and/or for internal mucosal application, comprising an effective amount of a sulfated polysaccharide; one or more of a metalloproteinase inhibitor, an anti-inflammatory agent, an acid pH control buffering system or any combination thereof; and a pharmaceutically acceptable carrier, further comprises one or more of a moisturizing agent, a chelating agent, a lubricant, a preservative or any combination thereof.

In some embodiments of the invention, the moisturizing agent is saccharide isomerate, aquaxyl (xlyltylglucoside, anhydroxyltol, xlyltol) or ammonium lactate, pyrolidonecarboxylic acid (PCA) and/or derivated esters (lauryl, isopropyl, benzyl) and/or sodium, potassium salts.

In some embodiments of the invention, the chelating agent is EDTA, Di & Tetra sodium, tetrasodium etidronate, sodium and/or potassium phosphate, polyphosphate and/or pyrophosphate salt.

In some embodiments of the invention, the composition further comprises flax seed extract.

In some embodiments of the invention, the composition further comprises chitosan.

In some embodiments of the invention, the composition of the invention further comprises a preservative. In some embodiments of the invention, the preservative is a natural preservative. In some embodiments of the invention, the preservative is one or more of a mixture of pentylene glycol, glyceryl caprylate and glyceryl undecylenate or monoester of caprylic acid and/or undecylenic acid, a mixture of caprilhydroxamic acid, caprylyl glycol, glycerin, caprylyl glycerin or any combination thereof.

In some embodiments of the invention, the composition for intravaginal and/or for internal mucosal application, comprising an effective amount of a sulfated polysaccharide; one or more of a natural quaternary polymer, a quaternary molecular compound, a metalloproteinase inhibitor, an anti-inflammatory agent, an acid pH control buffering system, or any combination thereof; and a pharmaceutically acceptable carrier, including one or more extracts of Green tea extract, Gotu Kola (*Centalla asiatica*) extract, Grape seed extract, *Chondrus Chrispus*, echinaccea, propolis, comfrey, melissa, grape fruit, mango seed, cranberry, cucumber, salvia, chamomile, aloevera, geranium, lavender, lemon, juniper, clove bud, lotus, moringa or any combination thereof.

In some embodiments of the invention, the composition for intravaginal and/or for internal mucosal application, comprising an effective amount of a sulfated polysaccharide; one or more of a metalloproteinase inhibitor, an anti-inflammatory agent, an acid pH control buffering system, or any combination thereof; and a pharmaceutically acceptable carrier further comprises water.

According to some embodiments, the composition for intravaginal and/or for internal mucosal application, comprising an effective amount of a sulfated polysaccharide; one or more of a metalloproteinase inhibitor, an anti-inflammatory agent, an acid pH control buffering system, or any combination thereof; and a pharmaceutically acceptable carrier.

According to some embodiments, the composition comprises sulfated polysaccharide is in an amount of 0.005-5% wt/wt of the solution. According to some embodiments, the composition comprises about 0.01-5.0% wt/wt sulfated polysaccharide.

According to further embodiments, the composition comprises about 0.1-3.0% wt/wt *Chondrus Chrispus* extract (silicone plant). According to further embodiments, the composition of the invention comprises about 1.0-5.0% wt/wt saccharide isomerate (plant derivative).

In some embodiments of the invention, the composition of the invention further comprises a lubricant. In some embodiments of the invention, the lubricant is a natural lubricant, comprises of Lubrasil-DM Hydrogel, glyceril polyacrylate, alginic acid, sodium salt, guar neutral, Xanthan gum or *Chondrus Chrispus*, sulfated polysaccharide, Guar gum, Hydroxypropyl Guar Hydroxypropyltrimonium Chloride or any combination thereof.

According to further embodiments, the composition comprises about 0.1-1.0% wt/wt sodium polyacrylate. According to further embodiments, the composition comprises about 0.1-1.0% wt/wt lubrasil DM hydrogel. It is noted that wt/wt is equivalent to w/w. According to further embodiments, the composition comprises about 0.1-1.0% w/w alginic acid. According to further embodiments, the composition comprises about 0.1-1.0% w/w sodium salt. According to further embodiments, the composition comprises about 0.1-1.0% w/w guar natural. According to further embodiments, the composition comprises about 0.1-1.0% w/w *Chondrus Chrispus*. According to further embodiments, the composition comprises about 1.0-1.5% wt/wt flax seed extract. According to further embodiments, the composition comprises about 0.02-0.04% wt/wt EDTA. According to further embodiments, the composition comprises about 0.02-0.04% wt/wt Di & Tetra sodium editronate. According to further embodiments, the composition comprises about 0.02-0.04% wt/wt sodium and/or potassium phosphate, pyrophosphate, and/or polyphosphate. According to further embodiments, the composition comprises about 0.3-2.0% wt/wt lactic acid and/or sodium lactate. According to further embodiments, the composition comprises about 0.5-1.0% wt/wt glyceryl caprylate. According to further embodiments, the composition comprises about 0.5-1.0% wt/wt monoesters of caprylic acid and undecylenic esters. According to further embodiments, the composition comprises about 0.1-2.0% wt/wt Hydroxypropyl Guar Hydroxypropyltrimonium Chloride. According to further embodiments, the composition comprises about 0.7-1.5% wt/wt of Lactic acid and Sodium dibasic hydrogen phosphate. According to further embodiments, the composition comprises about 0.01-1.0% wt/wt of at least one of Green tea extract, Gotu Kola (*Centalla asiatica*) extract, and/or Grape seed extract, melissa, grape fruit, mango seed, cranberry, allantoin, cucumber, salvia, chamomile, aloevera, caprylhydroxamic acid, caprylyl glycol and glycerin, or of their various combinations. According to further embodiments, the composition comprises about 0.5-2% of Pentylene Glycol, Glyceryl Caprylate and Glyceryl Undecylenate. According to further embodiments, the composition comprises about 0.1-2% of Xanthan gum. According to further embodiments, the composition comprises about 0.01-2% of Chitosan. According to further embodiments, the composition comprises about 0.1-2% of Allantoin.

According to further embodiments, the composition comprises about 0.01-1.0% w/w of one or more natural extracts, such as Green tea (*Camellia sinensis*) extract, Gotu Kola (*Centalla asiatica*) extract, Grape seed extract, echinaccea, comfrey, melissa, propolis, mango seed, grape fruit, cucumber, cranberry, chamomile, salvia, geranium, lavender, lemon, juniper, clove bod, lotus, moringa, resveratrol, or any combination thereof. In some embodiments of the invention, resveratrol may be added to the composition.

In some embodiments of the invention, the composition further comprises water.

In some embodiments of the invention, the composition further comprises a vitamin, such as for example, without limitation, vitamin E.

In some embodiments of the invention, the composition further comprises a chitosan.

In some embodiments of the invention, the sulfated polysaccharide is derived from alga. In an embodiment of the invention, the alga is a red alga, a green alga, a brown alga and/or *Chondrus Chrispus*

In one aspect, this invention provides a composition for intravaginal application, comprising an effective amount of at least one red, green or brown alga sulfated polysaccharide.

In some embodiments, the term "red microalga/e" or "red alga/e" is to be understood to encompass any of the 6,500 to 10,000 known species (W. J. Woelkerling (1990). "An introduction". In K. M. Cole & R. G. Sheath. *Biology of the Red Algae*. Cambridge University Press, Cambridge. pp. 1-6; M. D. Guiry. "Rhodophyta: red algae". National University of Ireland, Galway. Archived from the original on 2007 May 4. Retrieved 2007 Jun. 28). Some examples of species and genera of red algae may include *Cyanidioschyzon merolae, Porphyridium Cruentum, Atractophora hypnoides, Gelidiella calcicola, Lemanea, Palmaria palmata, Schmitzia hiscockiana, Chondrus crispus, Mastocarpus stellatus*, or *Acrochaetium efflorescens*. In an embodiment of the invention, the sulfated polysaccharide is derived from *Porphyridium* SP, *Porphyridium Cruentum* or *porphyridium purpureum*.

Red microalga sulfated polysaccharides, in some embodiments, are obtained from the cell walls by different procedures, e.g., by extraction. In some embodiments, the polysaccharide is secreted by the alga into the growth medium, and then utilized.

In some embodiments, the red microalga are grown as described in U.S. Pat. No. 5,534,417 (fully incorporated by reference herein), and the sulfated polysaccharides are isolated therefrom, using established methods.

In some embodiments of the invention, the extraction of the sulfated polysaccharide is carried out in the presence of ethyl alcohol and the sulfated polysaccharide of the present invention may be selectively extracted with an aqueous solvent, which in some embodiments, is conducted in the presence of 5-40% wt/wt ethyl alcohol or, in some embodiments, 8-15% wt/wt ethyl alcohol.

In some embodiments of the invention, the temperature for extracting the sulfated polysaccharide of the present invention is 50° C. or lower and in some embodiments, 15-30° C.

In some embodiments of the invention, the extraction may be carried out with stirring and in some embodiments; it is carried out under a non-shearing condition whereby the sulfated polysaccharide of the present invention can be efficiently prepared.

In some embodiments of the invention, if the extract is contaminated with impurities such as neutral sugars and proteins, then in some embodiments, removal of neutral sugars can be easily achieved by means known in the art such as ultrafiltration where the excluding molecular weight is about 100,000 or less. In some embodiments, removing the proteins, i.e. by treatment with protease, etc. may be used.

In other embodiments, the sulfated polysaccharide may be treated with endo-sulfated polysaccharide degrading enzyme, which in turn may liberate specific, desired sulfated saccharide products.

In some embodiments, the compositions of this invention are distinguished in that they contain highly sulfated polysaccharides. According to this aspect, and in some embodiments, the red, brown or green alga sulfated polysaccharide is characterized by a percent sulfation of between 0.01-35% of the polysaccharide chain. In some embodiments of the invention the percent sulfation is between 20-35% of the polysaccharide chain. In some embodiments of the invention the percent sulfation is between 0.1-20% of the polysaccharide chain. In some embodiments of the invention the percent sulfation is between 0.1-10% of the polysaccharide chain. In some embodiments of the invention the percent sulfation is between 1-10% of the polysaccharide chain. In some embodiments of the invention the percent sulfation is between 2-10% of the polysaccharide chain. In some embodiments of the invention the percent sulfation is between 2-11% of the polysaccharide chain. In some embodiments of the invention the percent sulfation is between 2-3% of the polysaccharide chain. In some embodiments of the invention the percent sulfation is between 3-4% of the polysaccharide chain. In some embodiments of the invention the percent sulfation is between 4-5% of the polysaccharide chain. In some embodiments of the invention the percent sulfation is between 5-6% of the polysaccharide chain. In some embodiments of the invention the percent sulfation is between 6-7% of the polysaccharide chain. In some embodiments of the invention the percent sulfation is between 7-8% of the polysaccharide chain. In some embodiments of the invention the percent sulfation is between 8-9% of the polysaccharide chain. In some embodiments of the invention the percent sulfation is between 9-10% of the polysaccharide chain. In some embodiments of the invention the percent sulfation is between 4-10% of the polysaccharide chain.

According to this aspect, and in some embodiments, the degree of sulfation of the polysaccharides for use in the compositions and methods of this invention provides a composition with sufficient activity.

In some embodiments, the composition of the invention may further comprise, inter-alia, a "drug" or "compound" or "agent", which refers in some embodiments, to a substance applicable for use in the treatment, prevention, alleviation, suppression, a delay in progression or reduction in incidence of a disease, disorder, condition or infection.

The compound, drug or agent may be one or more of an antimicrobial, an antiviral, an antifungal, an anti-inflammatory, anti-irritating, anti-itching, a hormone or a spermicidal compound or any other compound that can treat or alleviate or prevent a condition associated with woman's health, such as vaginitis, vulivitis, vestibulitis, vulvadynia, vulval itching or vulvavaginitis, vaginal atrophy, sexually transmitted diseases, vaginal atrophy and/or dryness following chemotherapy or during hormone therapy (adjuant, neoadjuvant or as the treatment itself) for cancer patients (such as aromatase inhibitors) and other local reproductive tract infections.

Sexually transmitted diseases, also referred to as sexually transmitted infections (STI) and venereal diseases (VD), are illnesses that have a significant probability of transmission between humans by means of human sexual behavior, including vaginal intercourse, oral sex, and anal sex.

In some embodiments, the sexually transmitted diseases which may be treated/prevented/alleviated by the compositions and methods of this invention include those of bacterial, viral, fungal, parasitic or protozoal in origin. In some embodiments, the sexually transmitted diseases which may be treated/prevented/alleviated by the compositions and methods of this invention include Chancroid (such as *Haemophilus ducreyi*), Chlamydia (such as *Chlamydia trachomatis*), Gonorrhea (such as *Neisseria gonorrhoeae*), Granuloma inguinale (such as *Klebsiella granulomatis*) or Syphilis (such as *Treponema pallidum*); Candidiasis; Viral hepatitis, Herpes simplex virus, HIV (Human Immunodeficiency Virus), HPV (Human Papillomavirus), Molluscum contagiosum (molluscum contagiosum virus MCV); Crab louse, (such as *Pthirus pubis*), Scabies (such as *Sarcoptes scabiei*), or Trichomoniasis (*Trichomonas vaginalis*).

In some embodiments, the added compound, drug or agent is a synthetic molecule and in some embodiments, the agent is a natural product. In some embodiments, the agent is a nucleic acid, a hormone, a growth factor, a cytokine, a chemokine, protein, an enzyme, a peptide, a drug, a label or a combination thereof.

In some embodiments, the composition of the invention may comprise, inter-alia, an antibody or antibody fragment, a peptide, an oligonucleotide, a ligand for a biological target, an immunoconjugate, a chemomimetic functional group, a glycolipid, a labelling agent, an enzyme, a metal ion chelate, an enzyme cofactor, a cytotoxic compound, a bactericidal compound, a bacteriostatic compound, a fungicidal compound, a fungistatic compound, a chemotherapeutic, a growth factor, a hormone, a cytokine, a toxin, a prodrug, an antimetabolite, a microtubule inhibitor, a radioactive material, a targeting moiety, or any combination thereof. In some embodiments, the drug, agent or compound may comprise, inter-alia, a peptide. In some embodiments, the term "peptide" refers to native peptides (either degradation products, synthetically synthesized peptides or recombinant peptides) and/or peptidomimetics (typically, synthetically synthesized peptides), such as peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, including, but not limited to, $CH_2$—NH, $CH_2$—S, $CH_2$—S=O, O=C—NH, $CH_2$—O, $CH_2$—$CH_2$, S=C—NH, CH=CH or CF=CH, backbone modifications, and residue modification. In one embodiment, the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" may include both D- and L-amino acids.

In some embodiments, the drug, agent or compound may comprise, inter-alia, an oligonucleotide, a nucleic acid, or a vector. In some embodiments, the term "oligonucleotide" is interchangeable with the term "nucleic acid", and may refer to a molecule, which may include, but is not limited to, prokaryotic sequences, eukaryotic mRNA, cDNA from eukaryotic mRNA, genomic DNA sequences from eukaryotic (e.g., mammalian) DNA, and synthetic DNA sequences. The term also refers to sequences that include any base analog of DNA and RNA.

In some embodiments, the composition is in the form of a gel, which in one embodiment is a hydrogel. In some embodiments of the invention, the composition may include hyaluronic acid, viscous agents such as, without being limited, microcrystalline cellulose, or chitosan.

In some embodiments of the invention, the composition is formulated in a form of a cream, an ointment, a solution, a gel, a suppository, an emulsion, foam, a capsule, a pill or a tablet.

In some embodiments, the drug, compound or agent may comprise, inter-alia, anticlotting agents, antihistamines, histamine, anti-inflammatory, agents that treat autoimmune disorder, antibacterial and antifungal agents, antibiotics, antiviral agents, anti-neoplastics, anticoagulants, androgens, corticoids, anabolic agents, growth hormone secretagogues, anti-infective agents, antiprotozoals, anesthetics, platelet inhibitors and glycogen phosphorylase inhibitors, diagnostic markers, drugs used for the control of birth, natural products, cell mediators, cell inhibitors, antimitotic agents, alkylating agents, immunomodulators, analgesics, vaccines, antimuscarinic and antispasmodic agents, immunosuppressive agents, vitamins, parasiticides or any combination thereof.

In some embodiments, the added compound, drug or agent may comprise, inter-alia, an anti-impotence agent, such as sildenafil citrate; anti-neoplastics, such as chlorambucil, lomustine or echinomycin; anti-inflammatory agents, such as betamethasone, prednisolone, piroxicam, aspirin, flurbiprofen and (+)-N-{4-[3-(4-fluorophenoxy)phenoxy]-2-cyclopenten-1-yl}-N-hyroxyurea; antivirals, such as acyclovir, nelfinavir, or virazole; vitamins/nutritional agents, such as retinol and vitamin E; an anticoagulant, such as dicumarol; androgens, such as 17-methyltestosterone and testosterone; a mineral corticoid, such as desoxycorticosterone; an antibiotic, such as ampicillin and penicillin G or belonging to the family of penicillines, cephalosporins, aminoglycosidics, macrolides, carbapenem and penem, beta-lactam monocyclic, inhibitors of beta-lactamases, tetracyclins, polipeptidic antibiotics, chloramphenicol and derivatives, fusidic acid, lincomicyn, novobiocine, spectinomycin, poly-etheric ionophores, quinolones; an anti-infective such as benzalkonium chloride or chlorhexidine; an antifungal such as econazole, terconazole, fluconazole, voriconazole or griseofulvin; an antiprotozoal such as metronidazole; an imidazole-type anti-neoplastic such as tubulazole; an anthelmintic agent such as thiabendazole or oxfendazole; an antihistamine such as astemizole, levocabastine, cetirizine, or cinnarizine; an anesthetic such as lidocaine; an antibacterial such as cotrimoxazole; a platelet inhibitor such as prostacyclin; a tetracycline antibiotic such as oxytetracycline or minocycline; a macrolide antibiotic such as azithromycin, clarithromycin, erythromycin or spiramycin; and glycogen phosphorylase inhibitors such as [R—(R*S*)]-5-chloro-N-[2-hydroxy-3{methoxymethyl-amino}-3-oxo-1-(phenylmethyl)-propyl]-IH-indole-2-carboxamide or 5-chloro-1-Hindole-2-carboxylic acid [(IS)-benzyl(2R)-hydroxy-3-((3R,4S)dihydroxy-pyrrolidin-1-yl-)-oxypropyl] amide.

In some embodiments, the drug, compound or agent may comprise, inter-alia, the anti-fungal fluconazole, the anti-inflammatory piroxicam and celicoxib and valdicoxib, and the antibiotics carbenicillin indanyl sodium, bacampicillin hydrochloride, troleandomycin, and doxycycline hyclate. In some embodiments, the drug, compound or agent may comprise, inter-alia, other antineoplastic agents such as platinum compounds (e.g., spiroplatin, cisplatin, and carboplatin), methotrexate, fluorouracil, adriamycin, mitomycin, ansamitocin, bleomycin, cytosine arabinoside, arabinosyl adenine, mercaptopolylysine, vincristine, busulfan, chlorambucil, melphalan (e.g., PAM, L-PAM or phenylalanine mustard), mercaptopurine, mitotane, procarbazine hydrochloride dactinomycin (actinomycin D), daunorubicin hydrochloride, doxorubicin hydrochloride, paclitaxel and other taxenes, rapamycin, manumycin A, TNP-470, plicamycin (mithramycin), aminoglutethimide, estramustine phosphate sodium, flutamide, leuprolide acetate, megestrol acetate, tamoxifen citrate, testolactone, trilostane, amsacrine (m-AMSA), asparaginase (L-asparaginase) Erwina asparaginase, interferon .alpha.-2a, interferon .alpha.-2b, teniposide (VM-26), vinblastine sulfate (VLB), vincristine sulfate, bleomycin sulfate, hydroxyurea, procarbazine, and dacarbazine; mitotic inhibitors such as etoposide, colchicine, and the vinca alkaloids, radiopharmaceuticals such as radioactive iodine and phosphorus products; hormones such as progestins, estrogens and antiestrogens; anti-helmintics, antimalarials, biologicals such as immune serums, antitoxins and antivenoms; bacterial vaccines; viral vaccines; blood products such as parenteral iron, hemin, hematoporphyrins and their derivatives; biological response modifiers such as muramyldipeptide, muramyltripeptide, microbial cell wall components, lymphokines (e.g., bacterial endotoxin such as lipopolysaccharide, macrophage activation factor), subunits of bacteria (such as Mycobacteria, Corynebacteria), the synthetic dipeptide N-acetyl-muramyl-L-alanyl-D-isoglutamine; anti-fungal agents such as ketoconazole, nystatin, griseofulvin, flucytosine (5-fc), miconazole, Amphotericin B, ricin, cyclosporins, and β-lactam antibiotics (e.g., sulfazecin); hormones such as growth hormone, estradiol, beclomethasone dipropionate, betamethasone, betamethasone acetate and betamethasone sodium phosphate, vetamethasone disodium phosphate, vetamethasone sodium phosphate, cortisone acetate, dexamethasone, dexamethasone acetate, dexamethasone sodium phosphate, flunisolide, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, paramethasone acetate, prednisolone, prednisolone acetate, prednisolone sodium phosphate, prednisolone tebutate, prednisone, triamcinolone, triamcinolone acetonide, triamcinolone diacetate, triamcinolone hexacetonide, fludrocortisone acetate, oxytocin, vassopressin, and their derivatives; vitamins such as cyanocobalamin neinoic acid, retinoids and derivatives such as retinol palmitate, and .alpha.-tocopherol; peptides, such as manganese super oxide dismutase; enzymes such as alkaline phosphatase; anti-allergic agents such as amelexanox; anti-coagulation agents such as phenprocoumon and heparin; antivirals such as amantadine azidothymidine (AZT, DDI, Foscarnet, or Zidovudine), ribavirin and vidarabine monohydrate (adenine arabinoside, ara-A); anticoagulants such as phenprocoumon, heparin; antibiotics such as dapsone, chloramphenicol, neomycin, cefaclor, cefadroxil, cephalexin, cephradine erythromycin, clindamycin, lincomycin, amoxicillin, ampicillin, bacampicillin, carbenicillin, dicloxacillin, cyclacillin, picloxacillin, hetacillin, methicillin, nafcillin, oxacillin, penicillin including penicillin G and penicillin V, ticarcillin rifampin and tetracycline; antiinflammatories such as diflunisal, ibuprofen, indomethacin, meclofenamate, mefenamic acid, naproxen, oxyphenbutazone, phenylbutazone, piroxicam, sulindac, tolmetin, aspirin and salicylates; antiprotozoans such as chloroquine, hydroxychloroquine, metronidazole, quinine and meglumine antimonate; antirheumatics such as penicillamine; local anesthetics such as bupivacaine hydrochloride, chloroprocaine hydrochloride, etidocaine hydrochloride, lidocaine hydrochloride, mepivacaine hydrochloride, procaine hydrochloride and tetracaine hydrochloride; anesthetics such as droperidol, etomidate, fentanyl citrate with droperidol, ketamine hydrochloride, methohexital sodium and thiopental sodium; and radioactive particles or ions such as strontium, iodide rhenium and yttrium.

In some embodiments, the drug, compound or agent may comprise, inter-alia, a molecule, which when provided to a subject in need, provides a beneficial effect. In some cases, the molecule is therapeutic in that it functions to replace an absence or diminished presence of such a molecule in a subject. In one embodiment, the molecule is a nucleic acid coding for the expression of a protein is absent, such as in cases of an endogenous null mutant being compensated for by expression of the foreign protein. In other embodiments, the endogenous protein is mutated, and produces a non-functional protein, compensated for by the expression of a heterologous functional protein. In other embodiments, expression of a heterologous protein is additive to low endogenous levels, resulting in cumulative enhanced expression of a given protein. In other embodiments, the molecule stimulates a signaling cascade that provides for expression, or secretion, or others of a critical element for cellular or host functioning.

In another embodiment, the compound, drug or agent may be a cytotoxic agent such as, for example, taxol, cytochalasin B, gramicidin D, ethidium bromide, emetine, mitomycin, etoposide, tenoposide, vincristine, vinblastine, colchicin, doxorubicin, daunorubicin, dihydroxy anthracinedione, mitoxantrone, mithramycin, actinomycin D, 1-dehydrotestosterone, glucocorticoids, procaine, tetracaine, lidocaine, propranolol, and puromycin and analogs or homologs thereof.

The compositions of the invention can be provided in any suitable vehicle. Thus, for instance, pharmaceutically-acceptable vehicles and/or carriers and/or adjuvants are contemplated for incorporation therein.

In some embodiments, the additional drug, compound or agent is effective as. In some embodiments, the additional drug, compound or agent is effective against vaginitis, vulivitis, vestibulitis, vulvadynia, vulval itching or vulvavaginitis.

In some embodiments of the invention, there is provided a use of a composition for intravaginal and/or for internal mucosal application, wherein the composition comprises an effective amount of a sulfated polysaccharide and a pharmaceutically acceptable carrier in the manufacture of a medicament for treating vaginal infection, vaginal dryness, vaginal or vulvo vaginal atrophy, vaginal itching, dyspareunia, vaginal or vulvar pain, vaginal or perivaginal inflammation or for promoting vaginal or wound healing and for treating vaginal atrophy/dryness/irritation during and/or following radiotherapy, chemotherapy or hormone therapy related to cancer (such as aromatase inhibitors).

In some embodiments, there is provided a method for treating vaginal infection, vaginal dryness, vaginal or vulvo vaginal atrophy, vaginal itching, dyspareunia, vaginal or vulvar pain, vaginal or perivaginal inflammation or for promoting vaginal or wound healing and for treating vaginal atrophy/dryness/irritation during and/or following chemotherapy or hormone therapy related to cancer (such as aromatase inhibitors) wherein the composition comprises an effective amount of a sulfated polysaccharide and a pharmaceutically acceptable carrier.

In some embodiments of the invention, there is provided a use of a composition for intravaginal and/or for internal mucosal application, wherein the composition comprises an effective amount of a sulfated polysaccharide and a pharmaceutically acceptable carrier in the manufacture of a medicament for treating or alleviating decreased vaginal boundary lubrication or a disease or condition associated therewith or of improving vaginal boundary lubrication.

In some embodiments of the invention, there is provided a method for treating or alleviating decreased vaginal boundary lubrication or a disease or condition associated therewith or of improving vaginal boundary lubrication comprising the step of vaginally administering a composition comprising an effective amount of a sulfated polysaccharide and a pharmaceutically acceptable carrier.

The disease or the condition associated with decreased vaginal boundary lubrication are typically vaginal atrophy, dyspareunia, Sjogren's syndrome, menopause, androgen deficiency, estrogen deficiency, estrogen replacement therapy, allergy, chronic inflammation, menopause, premature menopause, chemotherapy, hormonal therapy for cancer patients (such as aromatase inhibitors), breastfeeding, surgical removal of the ovaries before menopause, genital lichen sclerosis, vulvodynia, bacterial vaginosis, herpes, candida, psoriasis, contact dermatitis, condylomata, or side effects of medications and aging.

In some embodiments of the invention, there is provided a use of a composition for intravaginal and/or for internal mucosal application, comprising an effective amount of a sulfated polysaccharide and a pharmaceutically acceptable carrier, in the manufacture of a medicament for preventing episiotomy or for treating tissue damages after episiotomy. In such a case for using the composition for preventing episiotomy, the composition of the administered a week, two weeks, three weeks or a month before the date of delivery of a newborn.

In some embodiments of the invention, there is provided a method for preventing episiotomy or for treating tissue damages after episiotomy comprising the step of vaginally administering a composition comprising an effective amount of a sulfated polysaccharide and a pharmaceutically acceptable carrier.

According to some embodiments, the sulfated polysaccharide is derived from alga. According to some embodiments, the alga is a red alga, green alga and/or a brown alga. According to further embodiments, the red alga is *Porphyridium* sp., *P. aerugineum, Porphyridium Cruentum, porphyridium purpureum, R. reticulata. Cyanidioschyzon merolae, Atractophora hypnoides, Gelidiella calcicola, Lemanea, Palmaria palmata, Schmitzia hiscockiana, Chondrus crispus, Mastocarpus stellatus*, and/or *Acrochaetium efflorescens*. The brown alga is in some embodiments, *Undaria pinnatifida, Laminaria saccharina, L. digitata, Fucus evanescens, F. serratus, F. distichus, F. spiralis, Ascophyllum nodosum* and/or *Fucus vesiculosus* and the green alga/cyanobacteria is in some embodiments *Prasinococcus capsulatus, Spirulina, Chlorella, Isochrysis* and/or *Dunaliella*.

In some embodiments of the invention, there is provided a use of a composition for intravaginal and/or for internal mucosal application, wherein the composition comprises an effective amount of a sulfated polysaccharide, one or more of a natural quaternary polymer, a quaternary molecular compound, a metalloproteinase inhibitor, an anti-inflammatory agent, an acid pH control buffering system or any combination thereof, and a pharmaceutically acceptable carrier in the manufacture of a medicament for treating vaginal infection, vaginal dryness, vaginal or vulvo vaginal atrophy, vaginal itching, dyspareunia, vaginal or vulvar pain, vaginal or perivaginal inflammation or for promoting vaginal or wound healing.

In some embodiments of the invention, there is provided a method for treating vaginal infection, vaginal dryness, vaginal or vulvo vaginal atrophy, vaginal itching, dyspareunia, vaginal or vulvar pain, vaginal or perivaginal inflammation or for promoting vaginal or wound healing comprising the step of vaginally administering a composition comprising an effective amount of a sulfated polysaccharide, one or more of a natural quaternary polymer, a quaternary molecular compound, a metalloproteinase inhibitor, an anti-inflammatory agent, an acid pH control buffering system or any combination thereof, and a pharmaceutically acceptable carrier.

In some embodiments of the invention, there is provided a use of a composition for intravaginal and/or for internal mucosal application, wherein the composition comprises an effective amount of a sulfated polysaccharide, one or more of a natural quaternary polymer, a quaternary molecular compound, a metalloproteinase inhibitor, an anti-inflammatory agent, an acid pH control buffering system or any combination thereof, and a pharmaceutically acceptable carrier, in the manufacture of a medicament for treating or alleviating decreased vaginal boundary lubrication or a disease or condition associated therewith or of improving vaginal boundary lubrication.

In some embodiments of the invention, there is provided a method for treating or alleviating decreased vaginal boundary lubrication or a disease or condition associated therewith or of improving vaginal boundary lubrication comprising the step of vaginally administering a composition comprising an effective amount of a sulfated polysaccharide, one or more of a natural quaternary polymer, a quaternary molecular compound, a metalloproteinase inhibitor, an anti-inflammatory agent, an acid pH control buffering system or any combination thereof, and a pharmaceutically acceptable carrier.

The disease or the condition associated with decreased vaginal boundary lubrication are typically vaginal atrophy, dyspareunia, Sjogren's syndrome, menopause, androgen deficiency, estrogen deficiency, estrogen replacement therapy, allergy, chronic inflammation, menopause, premature menopause, chemotherapy, radiotherapy, hormonal treatment for cancer patients (aromatase inhibition), breast-feeding, surgical removal of the ovaries before menopause, genital lichen sclerosis, vulvodynia, bacterial vaginosis, herpes, candida, psoriasis, contact dermatitis, condylomata, or side effects of medications and aging.

In some embodiments of the invention, there is provided a use of a composition for intravaginal and/or for internal mucosal application, wherein the composition comprises an effective amount of a sulfated polysaccharide, one or more of a natural quaternary polymer, a quaternary molecular compound, a metalloproteinase inhibitor, an anti-inflammatory agent, an acid pH control buffering system or any combination thereof, and a pharmaceutically acceptable carrier, in the manufacture of a medicament for preventing episiotomy or for treating tissue damages after episiotomy. In such a case for using the composition for preventing episiotomy, the composition of the administered a week, two weeks, three weeks or a month before the date of delivery of a newborn.

In some embodiments of the invention, there is provided a use of a composition for intravaginal and/or for internal mucosal application, wherein the composition comprises an effective amount of a sulfated polysaccharide, one or more of a natural quaternary polymer, a quaternary molecular compound, a metalloproteinase inhibitor, an anti-inflammatory agent, an acid pH control buffering system or any combination thereof, and a pharmaceutically acceptable carrier, in the manufacture of a medicament for preventing and treating vaginal atrophy in cancer patients as a results of chemotherapy or hormonal treatment (drugs that blocks estrogen receptors, treatments that lower estrogen level such as aromatase inhibitiors and progesterone-like drugs). When using the composition for preventing chemotherapy or hormonal therapy associated conditions, the composition may be administered during and/or following the chemotherapy/hormonal therapy.

In some embodiments, the composition may be used in the manufacture of a medicament for preventing or for treating tissue damages associated with chemotherapy or hormonal therapy for cancer patients treated with drugs that block estrogen receptors, lowering estrogen level or progesterone-based agents.

In some embodiments the hormonal therapy for cancer patients include use of aromatase inhibitors. In some embodiments, the composition is used to cure the tissue damages caused by the hormonal therapy.

In some embodiments of the invention, there is provided a method for preventing episiotomy or for treating tissue damages after episiotomy comprising the step of vaginally administering a composition comprising an effective amount of a sulfated polysaccharide, one or more of a natural quaternary polymer, a quaternary molecular compound, a metalloproteinase inhibitor, an anti-inflammatory agent, an acid pH control buffering system or any combination thereof, and a pharmaceutically acceptable carrier.

Using formula on a daily basis up to one month before delivery date will hydrate and soften the cervix orifice and birth canal allowing it to expend and become elastic enough to avoid episiotomy and allow faster wound healing process after episiotomy.

According to some embodiments, the sulfated polysaccharide is derived from alga. According to some embodiments, the alga is a red alga, green alga and/or a brown alga. According to further embodiments, the red alga is *Porphyridium* sp., *P. aerugineum, Porphyridium Cruentum, porphyridium purpureum, R. reticulata. Cyanidioschyzon merolae, Atractophora hypnoides, Gelidiella calcicola, Lemanea, Palmaria palmata, Schmitzia hiscockiana, Chondrus crispus, Mastocarpus stellatus*, and/or *Acrochaetium efflorescens*. The brown alga is in some embodiments, *Undaria pinnatifida, Laminaria saccharina, L. digitata, Fucus evanescens, F. serratus, F. distichus, F. spiralis, Ascophyllum nodosum* and/or *Fucus vesiculosus* and the green alga/cyanobacteria is in some embodiments *Prasinococcus capsulatus, Spirulina, Chlorella, Isochrysis* and/or *Dunaliella.*

In some embodiments, this invention provides a use of a composition as herein described, in the manufacture of a medicament for treating vaginal or perivaginal inflammation or promoting vaginal or perivaginal wound healing.

In some embodiments, according to these aspects, use of the compositions of this invention in the preparation of a medicament for treating or promoting healing of episiotomy is specifically contemplated. In some embodiments of the invention, the composition may be used for the prevention of episiotomy.

In some embodiments, according to these aspects, use of the compositions of this invention in the preparation of a medicament for treating or promoting healing of vaginal dryness during or following chemotherapy or hormonal treatment for cancer patients is specifically contemplated. In some embodiments of the invention, the composition may be used to alleviate vaginal dryness associated with chemotherapy or hormonal therapy related to cancer. Hormonal treatment for cancer patient can be used as adjuvant, neoadjuvant or as the treatment itself. The treatments include drugs that block estrogen receptors (such as Tamoxifen, Fulvestrant), lowering estrogen level (Aromatase inhibitors) or progesterone-based therapy. In order to alleviate chemotheraphy and/or hormonal therapy-associated damage, the composition of the invention is administered during or at the end of the chemotherapy/hormonal treatment.

According to some embodiments of the invention, there is provided a use of a composition of the invention, in the manufacture of a medicament for treating or alleviating at least one menopause-associated symptom in a female patient.

The compositions of the invention are used for managing vaginal lubrication and to protect the vaginal epithelium against shear forces (including significant shear forces) and discomfort generated from the undesirable conditions including, for example, vaginal atrophy, dyspareunia, Sjogren's syndrome, androgen deficiency, estrogen deficiency, estrogen replacement therapy, allergy, chronic inflammation, menopause, premature menopause, chemotherapy, breastfeeding, surgical removal of the ovaries before menopause, genital lichen sclerosis, vulvodynia, bacterial vaginosis, herpes, candida, psoriasis, contact dermatitis, condylomata, side effects of medications and aging. Symptoms or indications of vaginal lubrication deficiency include, by way of non-limiting example, vaginal dryness, vaginal itch or a burning sensation, painful sexual intercourse, and light vaginal bleeding after intercourse.

According to some embodiments of the invention, there is provided a use of the composition of the invention in the manufacture of a medicament for treating or alleviating decreased vaginal boundary lubrication or a disease associated therewith or of improving vaginal boundary lubrication.

The disease or the conditions associated with decreased vaginal boundary lubrication is vaginal atrophy, dyspareunia, Sjogren's syndrome, menopause, androgen deficiency, estrogen deficiency, estrogen replacement therapy, allergy, chronic inflammation, menopause, premature menopause, chemotherapy, breastfeeding, surgical removal of the ovaries before menopause, genital lichen sclerosis, vulvodynia, bacterial vaginosis, herpes, candida, psoriasis, contact dermatitis, condylomata, or side effects of medications and aging.

A deficiency, as well as an improvement in vaginal lubrication and symptoms associated therewith can be determined by any suitable method. For example, qualitatively (e.g., a feeling of low lubrication, discomfort, vaginal dryness, vaginal itch or a burning sensation, painful sexual intercourse, and light vaginal bleeding after intercourse etc.) or quantitatively (e.g., measured through mechanical, histological, PAP smear, biochemical, electrical, optical, questionnaires) or any other method.

In some embodiments of the invention the composition is designed as a gel. The amount of the gel that is administered to the subject is between 1-5 ml per dose. In some embodiments of the invention the amount is 2.5-4.0 ml per dose.

In some embodiments of the invention, the composition of the invention is administered once, twice or three times a week or more. In some embodiments of the invention, the composition of the invention is administered once, twice or three times a day or more. In some embodiments of the invention, the composition is administered for a week, two weeks, month, six months or more.

In some embodiments of the invention, the composition of the invention is used for preventing episiotomy or for treating tissue damages after episiotomy. In order to prevent episiotomy, the composition of the invention is administered a week, two weeks, three weeks or a month before the date of delivery of the newborn.

In some embodiments of the invention, the composition of the invention is used for preventing or for treating tissue damages during and/or after chemotherapy or hormone therapy (adjuvant, neoadjuvant or as the treatment itself) for cancer patients treated with drugs that block estrogen receptors (such as Tamoxifen, Fulvestrant), lowering estrogen level (Aromatase inhibitors) or progesterone-based therapy. In order to alleviate chemotherapy and/or hormonal therapy-associated damage, the composition of the invention is administered during or at the end of the chemotherapy/hormonal treatment.

Determination of a therapeutically effective amount in the method of treating and the use described herein is well within the capability of those skilled in the art, and depends on the severity of the disease, its type, the mode of administration and the like.

For any preparation used in the methods of the invention, the therapeutically effective amount or dose can be estimated initially from in vitro other assays known in the art. Toxicity and therapeutic efficacy of the active ingredients described herein can be determined by standard pharmaceutical procedures in vitro or in-vivo, in cell cultures, experimental animals or on skin of healthy volunteers. The data obtained from these in vitro and cell culture assays, animal and human studies can be used in formulating a range of dosage for use in humans. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to ensure levels of the active ingredient are sufficient to induce or suppress the biological effect (minimal effective concentration, MEC). The MEC will vary for each preparation, but can be estimated from in vitro/in-vivo data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

EXAMPLES

Example 1

Comparing a Preparation of Sulfated Polysaccharide

A study will be conducted on about 30 women aged 50-75 suffering from post-menopausal conditions which include one or more of vaginal surface irritation, burning during urination, dyspareunia, intermittent light bleeding after intercourse, inflamed vaginal epithelium, with patchy erythema, petechiae, or increased friability, or a minimal or a significant vulvar lesion, or a thin endometrium of around 4 mm in width, or appearance of thin, pale vaginal walls that can be determined by a pelvic examination.

The women will be subjected to once a day or twice weekly treatment with the composition detailed in Table I or II with possible modifications below for about 45 days. A certain percentage of the participants will receive a placebo. The participant condition will be evaluated by doctors. Further, each participant will complete a questionnaire regarding their symptoms of urogenital atrophy. An improvement in one or more of the symptoms will be determined. In certain instances, the symptoms will be completely alleviated, or improved from severe to tolerable.

TABLE I

| Ingredient | Proposed % | Function |
| --- | --- | --- |
| Sulfated polysaccharide | 0.10-3.00 | Anti-Irritant, anti-Bacterial, Vaginal Care |
| Condrus Crispus Extract (plant silicone) | 0.10-3.00 | Anti-Irritant, Hydration, Film Forming, Lubricant |
| Saccaride Isomerate (100% Plant derivate) | 1.00-5.00 | Moisturizer |
| Sodium Polyacrylate | 0.10-1.00 | Viscosity Modifier Lubricant, Texturizer |
| Lubrasil DM Hydrogel | 0.10-1.00 | Viscosity Modifier Lubricant, Texturizer |
| Flax Seed Extract | 1.00-1.50 | Biofunctional, cosmobiotic, with probiotic effect. Normalizes natural microflora |
| Isoflavone aglycone (soy aglycon) | 1.00-5.00 | Collagen Booster Metalloproteinases inhibitor |
| Sodium Carboxymethyl Betaglucan | 0.02-0.10 | Immune-enhancing, increases self protecting capacity |
| EDTA | 0.02-0.04 | Chelating Agent |
| Lactic Acid/Sodium Lactate | 0.30-1.00 | Acid pH control (3.8-4.5) buffering system |

TABLE I-continued

| Ingredient | Proposed % | Function |
| --- | --- | --- |
| Monoesters of Caprylic and/or Undecylenic Acids and/or Caprylhydroxamic acid and/or Caprylyl Glycol Glycerin | 0.50-1.00 | Multi-functional, all-natural system for preservative free and self-preserving. Biostatic activity |
| Natural extracts, Echinaccea, Propolis, Comfrey, Melissa Grape Fruit, Mango Seed, Cranberry, Cucumber, Green Tea, Salvia, Chamomile, Geranium, Lavender, Lemon, Juniper, Clove Bud, Lotus, Moringa, Water | 1.00-50.00, Each one or different mixtures thereof. | According to the specific function requested |

TABLE II

| Ingredient | Proposed % | Function |
| --- | --- | --- |
| Water | 80-97% | |
| Sulfated polysaccharide | 0.05-3.00 | Anti-Irritant, anti-Bacterial, Vaginal Care |
| hydroxypropyltrimonium hydrolyzed proteins/beta glucan hydroxypropyltrimonium chloride/Hydroxypropyl Guar Hydroxypropyltrimonium Chloride/Berberine | 0.1-5 | quaternary molecular compound |
| Lactic Acid/Sodium Lactate And Sodium dibasic hydrogen phosphate | 0.5-2 | Acid pH control (3.8-4.5) buffering system |
| Natural extracts: Green Tea/Grape seed/Gotu Kola (centella asiatica)/ Chondrus Chrispus/melissa/ grape fruit/mango seed/ cranberry/cucumber/salvia/ chamomile/aloevera, Water | 0.1-3 Each one or different mixtures thereof. | According to the specific function requested |
| Pentylene Glycol, Glyceryl Caprylate, Glyceryl Undecylenate | 0.5-1.5 | PRESERVATIVE |
| Chitosan | 0.01-2% | Moisturizing |

Example 2

Determination of Water Retention of a Composition Comprising a Sulfated Polysaccharide Determination of transepidermal loss (TEWL) and/or skin hydration (measured by Corneometer) in 5-50 participants of a composition described in Table I or Table II with or without a quaternary molecular compound, will be performed to exhibit the increased efficacy of the quaternary molecular compound combined with the sulfated polysaccharide to reduce TEWL.

The compositions described in Table I or Table II with or without the quaternary molecule will be measured for skin hydration by Corneometer to determine the increased efficacy of the formulation containing quaternary molecular combined with the sulfated polysaccharide versus the sulfated polysaccharide alone Example 3

An In-Vitro Test for Evaluation of a Formula of Sulfated Polysaccharide for Treating Irritation and Inflammation An in-vitro test for evaluation of the metalloproteinase inhibition activity and the immune activity of one or more of: Green tea extract, Gotu Kola (*Centalla asiatica*) extract, Grape seed extract, *Chondrus Chrispus*, melissa, grape fruit, mango seed, cranberry, cucumber, salvia, chamomile, aloevera with or without the sulfated polysaccharide for treating irritation and inflammation will be conducted. A polysaccharide of red micro alga and the extracts indicates above will be applied to a keratinocyte or immune cell line and will be measured as MMP inhibitors and cytokine inhibitors.

Different combinations of sulfated polysaccharide will be prepared by mixing it with either Green tea extract, Gotu Kola (*Centalla asiatica*) extract, Grape seed extract, *Chondrus Chrispus*, melissa, grape fruit, mango seed, cranberry, cucumber, salvia, chamomile or aloevera w/w % ranging between about 0.001-1.0%. Each mixture will be put in a petri dish containing keratinocyte cells. The anti-inflammatory effect and the tissue repair activity of the compound as well as the synergistic effect of such compounds together with the sulfated polysaccharide will be measured to exhibit elevated/synergistic anti-inflammatory, and tissue repair activity.

Example 4

Use of a Composition Comprising Sulfated Polysaccharides for Treating Deficient Vaginal Boundary Lubrication in a Cancer Patient Treated with Chemotherapy and/or Hormonal Treatment (Aromatase Inhibitor)

A study will be conducted on about 40 women aged 20-75 with breast cancer, treated with aromataz inhibitors suffering from vaginal atrophy, which include one or more of vaginal surface irritation, burning during urination, dyspareunia, intermittent light bleeding after intercourse, inflamed vaginal epithelium, with patchy erythema, petechiae, or increased friability, or a minimal or a significant vulvar lesion, or a thin endometrium of around 4 mm in width, or appearance of thin, pale vaginal walls that can be determined by a pelvic examination.

The women will be subjected to once a day or twice weekly treatment with the composition detailed in Table I or Table II for about 60 days. Each participant will complete a questionnaire regarding their symptoms of urogenital atrophy.

An improvement in one or more of the symptoms will be determined. In certain instances, the symptoms will be completely alleviated, or improved from severe to tolerable when treated with the composition detailed in Table I or Table II.

Example 5

Assessment of the Synergistic Effect Between the Sulfated Polysaccharide and Natural Botanic Extract in Treating Irritation & Inflammation The ability of the sulfated polysaccharide in combination with one or more of the compounds: Green tea extract, Gotu Kola (*Centalla asiatica*) extract, Grape seed extract, *Chondrus Chrispus*, melissa, grape fruit, mango seed, cranberry, cucumber, salvia, chamomile, aloe vera will be measured in patch test study with irritation conducted by SLS. The skin of 5-50 subjects will be irritated with SLS and skin coloration (redness) will be measured. Optional: TEWL will be measured as well as an indicator for barrier function and integrity.

The formulation was assessed in patch test on 50 test subjects: 27 normal healthy, 6 eczema, 4 allergy and 13 subjects with sensitive skin. The product was applied to the back of panellists for a period of 48 hours. proper adherence of the test patches was assured by the inclusion of sodium dodecyl sulphate (SDS) in one concentration (1%) as a positive control. Water was used as a negative control. The treatment sites were assessed for the presence of irritation by a trained evaluator using a point visual scale at 48 h (30 min after patch removal) and 72 h after patch application. Results: no erythema, scaling or fissure was seen in all 50 subjects measured (data not shown).

Example 6

Comparing the Water Retention Ability of a Formulation Containing Sulfated Polysaccharides Alone and Sulfated Polysaccharides Combined with a Quaternary Molecule Two formulations, one comprising a quaternary molecule combined with the sulfated polysaccharides Fucoidan, extracted from *Undaria pinnatifida* (Brown alga) and the sulfated polysaccharide extracted from *porphyridium Cruentum* (Red alga), and the other comprising only the sulfated polysaccharides, were combined in the gels described in Table III or Table IV, detailed below. A control formulation, containing neither the quaternary molecule, nor the sulfated polysaccharides was also prepared. The gels were weighed on an analytical scale and the equivalent weight from each formulation was placed in an incubator. A sample from each gel was removed of the incubator at different time points and was measured using an analytical scale to prove that the gel containing the quaternary molecule retains more water. The gels were dried and weighed again. It is noted that unless explicitly mentioned otherwise, the sulfated polysaccharides related to herein are the Fucoidan extracted from *Undaria pinnatifida* (Brown alga) and the sulfated polysaccharide extracted from *porphyridium Cruentum* (Red alga).

Particularly, the following three formulation were prepared:

FAB03: sulfated polysaccharides (*Fuicodan* and *Porphyridium* polysaccharides) only (not including the quaternary molecule guar hydroxypropyltrimonium chloride)

FAB06: sulfated polysaccharides, and the quaternary molecule guar hydroxypropyltrimonium chloride FAB07: Control (no sulfated polysaccharides, or guar hydroxypropyltrimonium chloride (quaternary molecule))

TABLE III

| Formulation number<br>Composition | FAB03<br>% W/W | FAB06<br>% W/W | FAB07<br>% W/W |
|---|---|---|---|
| FUICODAN:<br>*Undaria pinnatifida* extract<br>(Brown alga) | 1 | 1 | 0 |
| SULFATED POLYSACCHARIDE<br>(Porphyridium polysaccharide) | 0.1 | 0.1 | 0 |
| Glyceryl Caprylate, Pentylene<br>Glycol, Glyceryl Undecylenate<br>(preservative) | 1 | 1 | 1 |
| Guar Hydroxypropyltrimonium<br>Chloride (quaternary molecule) | 0 | 2 | 0 |

TABLE III-continued

| Formulation number<br>Composition | FAB03<br>% W/W | FAB06<br>% W/W | FAB07<br>% W/W |
|---|---|---|---|
| Green Tea Extract | 0.1 | 0.1 | 0 |
| Xanthan gum | 1.8 | 0 | 1.8 |
| Lactic acid | 1 | 1 | 1 |
| Allantoin | 0.2 | 0.2 | 0.2 |
| Sodium dibasic hydrogen phosphate | 0.2 | 0.2 | 0.2 |
| Purified water | 94.6 | 94.4 | 95.8 |
| Total | 100 | 100 | 100 |

Procedure

Water-Release Rate at 24° C.

Approximately 100 mg of each sample were transferred to a separate weighed and labeled dish. The dishes were subsequently covered and weighed. Once the incubator/oven was preheated to 24° C., the samples were uncovered and placed in the incubator/oven. After four hours, the oven was opened and the sample dishes therein were covered quickly. The dishes were then transferred to a desiccator, and let to cool to room temperature for 15 minutes, after which they were weighed. The above procedure was repeated after 8 and 24 hours.

Results—24° C.

TABLE IV

| | Water loss (%)-24 hr | | |
|---|---|---|---|
| Hr | FAB03-No Guar hydroxypropyltrimonium chloride (quaternary molecule) | FAB06-Including Guar hydroxypropyltrimonium chloride (quaternary molecule) | FAB07-Control |
| 0 | 0 | 0 | 0 |
| 4 | 94.9 | 77 | 96.2 |
| 8 | 94.8 | 92.2 | 96.5 |
| 24 | 93.9 | 92.6 | 96.4 |

Figure 2:
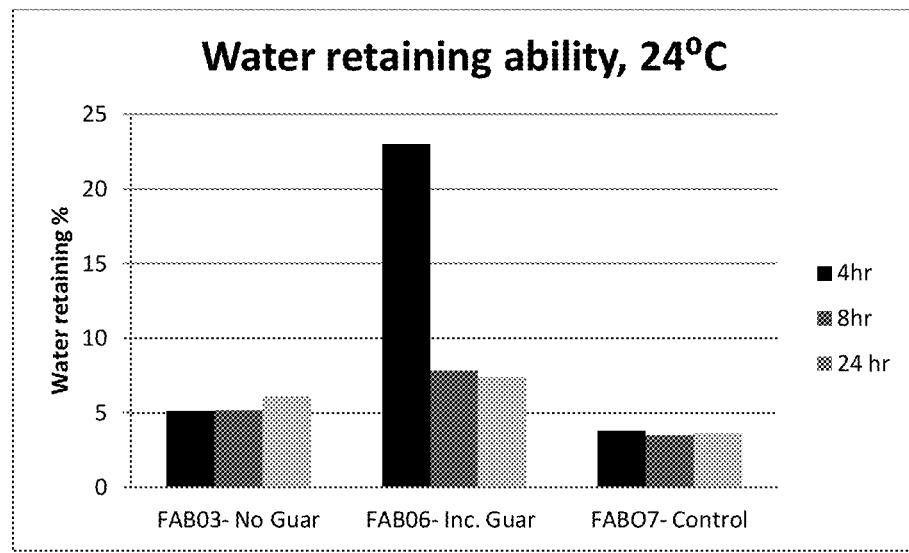
FIG. 2 presents the water retention of the same three formulations as measured at three different time points, after incubation at 24° C.

FIGS. 1 and 2 present the water loss and water retention results after 4, 8 and 24 hour of incubation at 24° C.

Particularly, FIG. 1 shows that the water loss of the FAB06 formulation, which included both sulfated polysaccharides extracted from the alga extracts (*Fuicodan* extracted from *Undaria pinnatifida*, and *Porphyridium* polysaccharides) as well as the quaternary molecule Guar Hydroxypropyltrimonium Chloride, presented the lowest water loss percentages at all times tested. Further, after four hours, the differences between the water loss of the FAB06 formulation and the other formulations are the largest. Further, the FAB03 formulation, containing only the alga extracts, not the quaternary molecule guar hydroxypropyltrimonium chloride, demonstrated a lower water loss than the FAB07 control at all times tested.

As presented in FIG. 2, the water retention ability was the highest in the FAB06 formulation. As further presented in FIG. 2, the water retention ability was higher in the FAB03 formulation in comparison to the FAB07 control.

CONCLUSIONS

From the comparison between the FAB03 and the FAB07 control formulations it appears that the sulfated polysaccharides (*Fuicodan* and *Porphyridium* polysaccharides) have water retention abilities, while the addition of a quaternary molecule (Guar Hydroxypropyltrimonium Chloride) further enhances the water retention abilities of the formulation, as shown when comparing the FAB06 formulation to the FAB03 and FAB07 formulations. The higher the water retention ability of the formulation, the lower the water loss and accordingly, the formulations providing high water retention present low water loss and vice versa.

It will be understood by those skilled in the art that various changes in form and details may be made therein without departing from the spirit and scope of the invention as set forth in the appended claims. Those skilled in the art will recognize, or be able to ascertain using no more than routine experimentation, many equivalents to the specific embodiments of the invention described herein. Such equivalents are intended to be encompassed in the scope of the claims.

What is claimed is:

1. A composition for intravaginal application, comprising 0.1% w/w fucoidan, 0.2% w/w *prasinococcus capsulatus* polysaccharide, 0.1 w/w *porphyridium* polysaccharide, 0.1% w/w chitosan, an acid pH control buffering system, a pharmaceutically acceptable carrier, and 0.1% w/w guar hydroxypropyltrimonium chloride, wherein the composition is in the form of a gel wherein the *porphyridium* polysaccharide consists of exo-polysaccharides derived from a *porphyridium* algae and wherein the *prasinococcus capsulatus* polysaccharide consists of exo-polysaccharides derived from a *prasinococcus capsulatus* algae.

2. The composition of claim 1, wherein said acid pH control buffering system is lactic acid, sodium dibasic hydrogen phosphate, sodium lactate, citric acid, or any combination thereof.

3. The composition of claim 1, wherein the composition further comprises one or more of saccharide isomerate as a moisturizing agent, and ethylenediaminetetraacetic acid (EDTA) as a chelating agent.

4. The composition of claim 1, wherein the composition further comprises one or more of extract of *Chondrus Chrispus*, Xanthan gum, caprylhydroxamic acid, caprylyl glycol, glycerin, undecylenic acid, monoester of caprylic acid, an extract of any one of echinaccea, propolis, comfrey, melissa, grape fruit, mango seed, cranberry, cucumber, salvia, Chamomile, Geranium, lavender, lemon, juniper, clove bud, lotus, moringa, Grape seed or Gotu Kola (*Centella asiatica* extracts) or any combination thereof.

5. The composition of claim 1, wherein said composition further comprises one or more of an antimicrobial, an antiviral, an antifungal, an anti-inflammatory, anti-irritating, anti-itching, growth factor, a hormone or a spermicidal compound.

6. The composition according to claim 1, wherein said composition further comprises one or more anti inflammatory agents.

* * * * *